United States Patent [19]

Wyvratt, Jr.

[11] Patent Number: 4,833,168
[45] Date of Patent: May 23, 1989

[54] AVERMECTIN REFORMATSKY ADDUCTS

[75] Inventor: Matthew J. Wyvratt, Jr., Mountainside, N.J.

[73] Assignee: Merck & Co., Inc., Rahway, N.J.

[21] Appl. No.: 914,891

[22] Filed: Oct. 3, 1986

[51] Int. Cl.$^4$ .................. A61K 31/365; C07D 311/96
[52] U.S. Cl. ..................................... 514/450; 519/261
[58] Field of Search ........................ 549/264; 519/264; 514/450

[56] References Cited

U.S. PATENT DOCUMENTS

| | | |
|---|---|---|
| 4,199,569 | 4/1980 | Chabala et al. |
| 4,201,861 | 5/1980 | Mrozik et al. |
| 4,206,205 | 6/1980 | Mrozik et al. |
| 4,310,519 | 1/1982 | Albers-Schonberg et al. |
| 4,478,760 | 10/1984 | Blancou et al. .................... 549/563 |

OTHER PUBLICATIONS

H. O. House, Modern Synthetic Reactions, second edition (1972), pp. 671–676.
LeGoff, *Journal of Organic Chemistry*, 29 2048 2050 (1964).

*Primary Examiner*—Richard L. Raymond
*Assistant Examiner*—Mark W. Russell
*Attorney, Agent, or Firm*—David L. Rose; Michael C. Sudol

[57] ABSTRACT

There are disclosed novel avermectin compounds wherein the glycosyl side chain is substituted with, or replaced by an alkyl ester group in a Reformatsky reaction. The compounds are prepared by reacting an α-halogenated ester to a 4'-, 4"- or 13-keto-avermectin derivative in the presence of a reducing agent. The avermectin compounds have utility as anti-parasitic agents and compositions for that use are also disclosed. The compounds are also highly potent insecticides against agricultural pests.

4 Claims, No Drawings

AVERMECTIN REFORMATSKY ADDUCTS

BACKGROUND OF THE INVENTION

The term avermectin (previously referred to as C-076) is used to describe a series of compounds isolated from the fermentation broth of an avermectin Producing strain of *Streptomyces avermitilis* and derivatives thereof. The morphological characteristics of the culture are completely described in U.S. Pat. No. 4,310,519. The avermectin compounds are a series of macrolides, each of which is substituted thereon at the 13-position with a 4'-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth have the following structure:

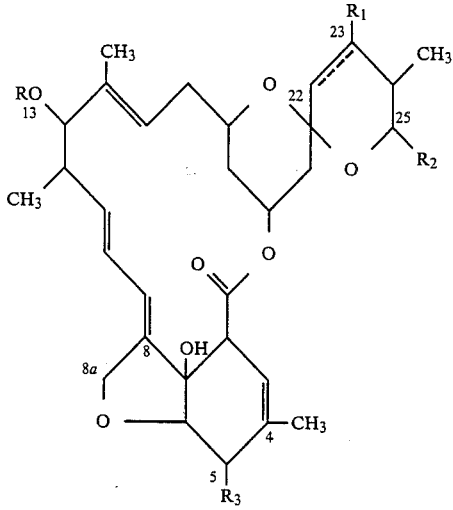

wherein R is the 4'-(α-L-oleandrosyl)-α-1-oleandrose group of the structure:

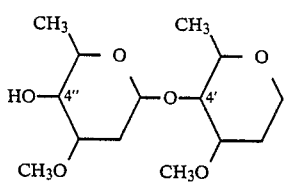

and wherein the broken line indicates a single or a double bond; $R_1$ is hydroxy and is present only when said broken line indicates a single bond;

$R_2$ is iso-propyl or sec-butyl; and $R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'-(α-L-oleandrosyl)-α-L-oleandrose):

| | $R_1$ (22,23-bond) | $R_2$ | $R_3$ |
|---|---|---|---|
| A1a | (Double Bond) | sec-butyl | —OCH$_3$ |
| A1b | (Double Bond) | iso-propyl | —OCH$_3$ |
| A2a | —OH | sec-butyl | —OCH$_3$ |
| A2B | —OH | iso-propyl | —OCH$_3$ |
| B1a | (Double Bond) | sec-butyl | —OH |
| B1b | (Double Bond) | iso-propyl | —OH |
| B2a | —OH | sec-butyl | —OH |
| B2b | —OH | iso-propyl | —OH |

The avermectin compounds are generally isolated as mixtures of a and b components. Such compounds differ only in the nature of the $R_2$ substituent and the minor structural differences have been found to have very little effect on the isolation procedures, chemical reactivity and biological activity of such compounds.

Hydrogenation at the 22,23-double bond of avermectin B1a and/or B1b or deoxygenation of the 23-hydroxy group of avermectin B2a and/or B2b gives 22,23-dihydro avermectin B1a and/or B1b, a mixture of which is known as ivermectin. Derivatives of these dihydro compounds are also used as starting materials for this invention.

SUMMARY OF THE INVENTION

The instant invention is concerned with certain derivatives of avermectin compounds wherein the 4' or 4"carbon atom of the glycosyl side chain or the 13-carbon of the aglycone compound is further substituted with an alkyl ester group. Thus it is an object of the instant invention to describe such avermectin Reformatsky derivatives. A further object is to describe processes for the preparation of such compounds. A still further object is to describe the uses of such compounds as anti-parasitic agents. Still further objects will become apparent from a reading of the following description.

DESCRIPTION OF THE INVENTION

The compounds of the instant invention have the following structural formula.

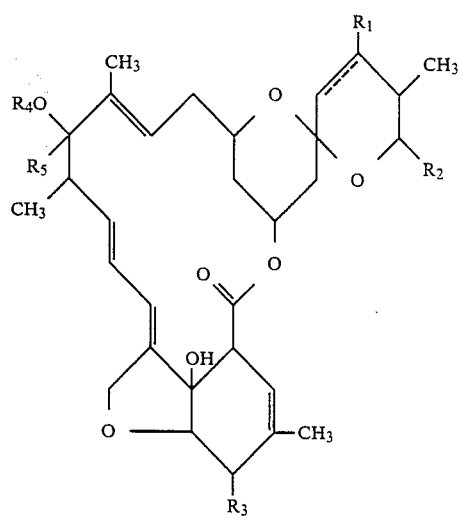

wherein the broken line indicates a single or double bond;

$R_1$ is H, =O, loweralkanoyloxy, or OH provided that $R_1$ is present only when the broken line indicates a single bond;

$R_2$ is isopropyl or sec-butyl;
$R_3$ is OH, OCH$_3$ or loweralkanoyloxy;
$R_4$ is H,

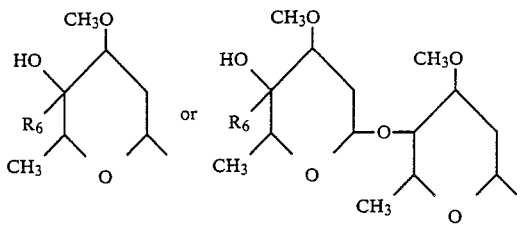

$R_5$ is hydrogen or $R_6$ provided that $R_5$ is hydrogen only when $R_4$ is other than hydrogen; and $R_6$ is $R_7O_2C$—$CH_2$—, $R_7O_2CCHF$—, $R_7O_2CCF_2$— or $R_7O_2CCH(Alk)$— where Alk is loweralkyl or phenyllower alkyl; and $R_7$ is hydrogen, loweralkyl, phenylloweralkyl, or substituted phenylloweralkyl wherein the substituents are loweralkyl or halogen;

and the tri(loweralkyl)silyl protected hydroxy derivatives thereof.

The term "loweralkyl" when used in the instant application is intended to represent those alkyl groups either straight or branched chain which have from 1-5 carbon atoms. Examples of such alkyl groups are methyl, ethyl, propyl, sec-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propionyl, butyryl, valeryl, and the like.

The term "halogen" is intended to include those halogen atoms fluorine, chlorine, bromine and iodine.

Examples of preferred compounds of the instant invention, and their physiologically acceptable salts, are:
4"-[(ethoxycarbonyl)methyl]avermectin B1a/B1b;
4"-[(ethoxycarbonyl)methyl]-22,23-dihydroavermectin B1a/B1b;
4"-[(ethoxycarbonyl)methyl]avermectin A1a/A1b;
4"-[(ethoxycarbonyl)difluoromethyl]avermectin B1a/B1b;
4'-[(ethoxycarbonyl)methyl]-22,23-dihydroavermectin B1a/B1b monosaccharide;
4'-[(ethoxycarbonyl)methyl]avermectin B2a/B2b;
13-[(ethoxycarbonyl)methyl]-22,23-dihydroavermectin B1a/B1b aglycone.

The avermectin "b" compounds, those with a 25-isopropyl group, are difficult to separate from the corresponding "a" compound with a 25-sec-butyl group and as such the compounds are generally isolated as mixtures of the two compounds. Thus references in the instant application to "a" compounds such as B1a, A1a, and the like, are construed to define the pure compound as well as those which actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like. If desired, the pure "a" (25-sec-butyl) and "b" (25-isopropyl) compounds can be obtained by chromatographic separation, such as with reversed phase, high performance liquid chromatography.

The compounds of this invention are prepared by treating a 4"-avermectin, 4'-avermectin monosaccharide or 13-avermectin aglycone keto compound with an α-haloester reagent, selected from $R_7O_2CCH_2Hal$, $R_7O_2CCHFHal$, $R_7O_2CCF_2Hal$, and $R_7O_2CCH(Alk)$-Hal in the presence of an activated form of zinc, preferably a zinc-copper couple, as a reducing agent where Hal represents a halogen, preferably bromine. The reaction is carried out by combining the keto-avermectin compound with an excess of the α-haloester in an organic solvent in the presence of an excess of the zinc-copper couple. Typical organic solvents are tetrahydrofuran, diglyme, diethylether, benzene, and the like. The reaction mixture is refluxed for from ½ to 12 hours, preferably for 2 to 6 hours and the product is isolated using techniques known to those skilled in the art.

The activated form of zinc is prepared by forming an alloy, also referred to as a "couple" with other metals such as copper or silver, preferably copper, as described in The Journal of Organic Chemistry 29, 2048 (1964) by E. LeGaff.

PREPARATION OF STARTING MATERIALS

The ultimate starting materials for the compounds of this invention are the avermectin fermentation products defined above. Thus it is apparent that additional reactions are required to prepare many of the starting materials for the instant compounds. Specifically, reactions are carried out at the 4'-, 4"-, 5-, 13-, 22-, and 23-positions. It is often necessary or desirable to protect hydroxy groups which are not intended for reaction, with the appropriate protecting groups known in the art. Other reactions may then be carried out without affecting the remainder of the molecule. Subsequently, the protecting group is removed and the unprotected product isolated. The protecting group employed is ideally one which may be readily synthesized, will not be affected by the reaction being carried out, and may be readily removed without affecting any other functions of the molecule. It is noted that the instant protected compounds are novel and have considerable antiparasitic activity. They are included within the ambit of the instant invention. One preferred type of protecting group for the avermectin type of molecule is the tri-substituted silyl group, preferably the trialkyl silyl group. One especially preferred example, is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours at from 0 to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions. If it is desired to protect the 23-hydroxy group a 4", 5,23-tri-(phenoxyacetyl) derivative can be prepared. Mild basic hydrolysis will leave the highly hindered 23-O-substituent but will hydrolize the 5- and 4"-O-phenoxy acetyl groups leaving them available for reaction. The 5-position may then be selectively protected as described above with t-butyldimethylsilyl, and the 4" group may then be reacted.

The silyl group may be removed after the other contemplated reactions may be carried out. The silyl group or groups are removed by stirring the silyl compound in methanol catalyzed by a catalytic amount of an acid, preferably a sulfonic acid such as p-toluene sulfonic acid. The reaction is complete in about 1 to 12 hours at from 0° to 50° C. The silyl group may also be removed using a hydrogen fluoride-pyridine complex in an organic solvent such as tetrahydrofuran. The reaction is complete in from 3 to 24 hours and is preferably carried out at room temperature.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the avermectin A1 and B1-series of compounds. Thus in the "1" series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

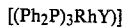

wherein

Ph is phenyl and Y is halogen. The reduction procedure is completely described in U.S. Pat. No. 4,199,569 to Chabala et al.

Additional reactions which may be carried out to prepare the compounds of this invention are the selective removal of one of the α-L-oleandrosyl moieties (described in U.S. Pat. No. 4,206,205 to Mrozik et al.) or the selective acylation of the susceptible hydroxy groups (described in U.S. Pat. No. 4,201,861 to Mrozik et al.).

The reaction conditions which are generally applicable to the preparation of the monosaccharide and aglycone involves dissolving the avermectin compound or the hydrogenated avermectin compound in an aqueous acidic non-nucleophilic organic solvent, miscible with water, preferably dioxane, tetrahydrofuran, dimethoxythane, dimethylformamide, bis-2-methoxyethyl ether, and the like, in which the water concentration is from 0.1 to 20% by volume. Concentrated acid is added to the aqueous organic solvent to the extent of 0.01 to 10% by volume. The reaction mixture is generally stirred at about 20°–40° C., preferably at room temperature, for from 6 to 24 hours. The lower concentration of acid, from about 0.01 to 0.1% will predominately produce the monosaccharide under the above reaction conditions. Higher acid concentrations, from about 1 to 10% will predominantly produce the aglycone under the above reaction conditions. Intermediate acid concentrations will generally produce mixtures of monosaccharide and aglycone. The products are isolated, and mixtures are separated by techniques such as column, thin layer preparative and high pressure liquid chromatography, and other known techniques.

The acids which may be employed in the above process include mineral acids and organic acids such as sulfuric, hydrohalic, phosphoric, trifluoroacetic, trifluoromethane sulfonic and the like. The hydrohalic acids are preferably hydrochloric or hydrobromic. The preferred acid in the above process is sulfuric acid.

A further procedure for the preparation of the monosaccharide of the avermectin compounds uses 1% concentrated sulfuric acid by volume in isopropanol at from 20°–40° C., preferably room temperature, for from 6 to 24 hours.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures. The acylation reactions are described completely in U.S. Pat. No. 4,201,861 to Mrozik et al.

The acylation reagents employed are generally the halide, preferably the chloride, of the above loweralkanoyl groups. That is the loweralkanoyl halide reagent is generally employed.

In addition, the acylation reagent could be in the form of the anhydride. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, dimethylamino pyridine, diisopropylethylamine and the like. The basic compound is required in equimolar amounts relative to the numbered moles of hydrogen halide being liberated, however excess amounts, even using the basic compound as a solvent, are not detrimental.

The 4''-, 4'-, 13- and/or 23-hydroxy groups are oxidized to the 4''-, 4'-, 13- and/or 23-keto groups respectively using oxidizing agents such as pyridinium dichromate; oxalylchloride-dimethylsulfoxide; acetic anhydride-dimethylsulfoxide; chromic acid-dimethylpyrazole; chromic acid; trifluoromethylacetic anhydride-dimethylsulfoxide; chromic acid-acetic acid; and the like. Oxalylchloride-dimethylsulfoxide (Swern oxidation) is the preferred oxidizing method. Suitably protected compounds, as described above, are employed. The reaction is carried out at from dry-ice bath temperatures to room temperature, preferably from dry-ice bath temperatures to 0° C. and is complete in from 1–24 hours. The reaction may be carried out in any solvent in which the starting materials are reasonably soluble, and which will not react with the oxidizing agent. Such solvents as dimethylformamide, dimethylsulfoxide, methylene chloride, chloroform, carbon tetrachloride and the like are acceptable. For pyridinium dichromate reactions, dimethylformamide and dimethylsulfoxide are preferred. For chromic acid-dimethylpyrazole reactions, methylene chloride is preferred. The compounds are isolated from the reaction mixture using procedures known to those skilled in the art.

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophaqostomum, Chabertia, Trichuris, Strongylus, Trichonema, Dictyocaulus, Capillaria, Haterakis, Toxocara, Ascaridia, Oxyurisn, Ancylostoma, Uncinaria, Toxascaris and Parascaris. Certain of these, such as Nematodirus. Cooperia and Oesphagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiases lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia. Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such 1 parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage, The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention In the isolation of the avermectin compounds, which serve as starting materials for the instant processes, from the fermentation broth, the various avermectin compounds will be found to have been prepared in unequal amounts. In particular an "a" series compound may be obtained in a higher proportion than the corresponding "b" series compound. The difference between the "a" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a small percent by weight, and this structural difference has negligible effect on the reaction processes and biological activities.

In particular it has been found that the starting materials for the compounds of this invention are very often prepared in a ratio of about 80% avermectin B1a or A1a and 20% avermectin B1b or A1b. Thus the preferred composition of this invention is one which contains about 80% of the "a" component and 20% of the "b" component.

The following examples are provided in order that this invention might be more fully understood; they are not to be construed as limitative of the invention.

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

EXAMPLE 1

4"-[(Ethoxycarbonyl)methyl]avermectin B1a/B1b

To a hot (90° C.) solution of copper (II) acetate monohydrate (15 mg) in 2 ml of glacial acetic acid in a 15 ml centrifuge tube was added 155 mg of powdered zinc. The mixture was stirred under nitrogen for 30 minutes and then centrifuged. The acetic acid solution was then decanted and the zinc-copper couple repeatedly washed with dry diethyl ether (3×6 ml). The couple was finally rinsed once with dry tetrahydrofuran (8 ml).

The semi-dry zinc-copper couple was transferred to a round-bottom flask under nitrogen. The couple was suspended in 5 ml of tetrahydrofuran. To this mixture, 74 mg of 4"-keto-avermectin B1and 35 µl of ethyl bromoacetate was added and the mixture heated at reflux. Additional ethyl bromoacetate was periodically added until thin layer chromatography indicated complete consumption of the starting ketone.

The reaction mixture was added to 50 ml of saturated ammonium chloride solution and 50 ml of ethyl acetate. The mixture was stirred for 20 minutes, filtered, and the layers separated. The aqueous layer was further extracted with ethyl acetate (2×20 ml). The combined organic layers were then washed with water and brine. The solution was dried with anhydrous sodium sulfate and concentrated to give 91 mg of crude product.

The crude product was purified by chromatography (3:2 ethyl acetate:hexanes) to give two epimeric products: Isomer A, 4 mg; Isomer B, 23 mg. Each isomer was identified by high field proton NMR studies in conjunction with mass spectroscopy results.

EXAMPLE 2

4'-[(Ethoxycarbonyl)methyl]-22,23-dihydroavermectin B1a/B1b Monosaccharide

To a suspension of the zinc-copper couple (prepared as in Example 1) in 2 ml of dry tetrahydrofuran, 100 mg of 4'-keto-5-O-(tert-butyldimethylsilyl)-22,23-dihydroavermectin B1monosaccharide and 13 µl of ethyl bromoacetate was added. The mixture was heated at reflux under nitrogen. Periodically, additional ethyl bromoacetate was added until thin layer chromatography indicated complete consumption of the starting ketone. The reaction mixture was filtered through a glass wool plug into 10 ml of saturated ammonium chloride solution. The aqueous mixture was extracted with ethyl acetate (3×20 ml). The combined organic layers were back-washed with water and brine, dried with sodium sulfate, and concentrated under reduced pressure to give 105 mg of crude product. Repeated chromatography (1:4 ethyl acetate:hexanes) on silica gel afforded two epimeric products: Isomer A, 11 mg; Isomer B, 38 mg. Each isomer was individually desilylated with 3 ml of 0.5% p-toluenesulfonic acid in methanol (1 hour, room temperature). The methanolic solution was added to 10 ml of sodium bicarbonate solution and extracted with ethyl acetate (3×15 ml). The combined ethyl acetate layers were washed with water and brine, dried with sodium sulfate, and concentrated to give crude product. Preparative thin layer chromatography on silica gel (1:2 ethyl acetate:dichloromethane) gave the pure products: Isomer A, 6.5 mg; Isomer B, 18 mg. Each isomer gave spectroscopic data consistent with its structure.

EXAMPLE 3

4''-[(Ethoxycarbonyl)difluoromethyl]avermectin B1a/B1b

To a suspension of the zinc-copper couple (prepared as in Example 1 from 286 mg of zinc dust and 16 mg of copper (II) acetate monohydrate) in 1 ml of dry tetrahydrofuran, 4''-keto-5-O-(tert-butyl dimethylsilyl)avermectin $B_1$ (207 mg) and ethyl bromodifluoroacetate (42 mg) were added. The reaction mixture was heated at reflux for 2.5 hours. Periodically, additional ethyl bromodifluoroacetate (5 additional equivalents) was added until 4''-keto-5-O-(tert-butyldimethylsilyl)avermectin $B_1$ was completely consumed as observed with thin layer chromatography (silica, 2:1 hexanes:ethyl acetate). The reaction mixture was added to 15 ml of saturated ammonium chloride solution and 15 ml of ethyl acetate. The resulting mixture was filtered through glass wool and the layers separated. The aqueous layer was further extracted with ethyl acetate. The organic layers were dried with sodium sulfate and concentrated to give 242 mg of crude product. Chromatography on silica gel (3:1 hexanes: ethyl acetate) afforded 44 mg of 4''-[(ethoxycarbonyl)difluoromethyl]-5-O-tert-butyldimethylsilyl)avermectin $B_1$ as a mixture of epimers at the $C_{4''}$ position. This mixture was then desilylated by dissolving in 1.5 ml of a stock solution of HF-pyridine in tetrahydrofuran (2 ml of commercial (Aldrich Chemical Co.) (HF)$_x$-pyridine diluted with 14 ml of dry tetrahydrofuran and 4 ml of dry pyridine). The mixture was stirred for 18 hours at room temperature under nitrogen. The reaction mixture was added to saturated sodium bicarbonate solution and then extracted with ethyl acetate. The organic layer was washed with 0.5N hydrochloric acid, water, 5% sodium bicarbonate solution, water and brine (in that order) and dried with sodium sulfate. Concentration gave 37.8 mg of crude product which was purified by preparative thin layer chromatography on silica gel (2:3 hexane:ethyl acetate) to give two isomers of 4''-[(ethoxycarbonyl)-difluoromethyl]avermectin $B_1$ Isomer A, 2 mg; Isomer B, 20.5 mg. Both isomers exhibited spectroscopic data consistent with these structures.

EXAMPLE 4

4''-[(Ethoxycarbonyl)methyl]-avermectin A1a/A1b

To a suspension of the zinc-copper couple (prepared as in Example 1) in 2 ml of dry tetrahydrofuran, 100 mg of 4''- keto-avermectin A1a/A1b and 15 μl of ethyl bromoacetate is added. The reaction mixture is heated at reflux under nitrogen. Additional ethyl bromoacetate is periodically added via syringe until reaction is judged to be complete by thin layer chromatography on silica gel. The heterogeneous reaction mixture is then filtered into 10 ml of saturated ammonium chloride solution. The aqueous mixture is then repeatedly extracted with ethyl acetate. The organic extracts are back-washed with water and brine and then dried with sodium sulfate. Concentration of this organic solution gives the crude product. Preparative thin layer chromatography on silica gel affords pure 4''-[(ethoxycarbonyl)methyl]-avermectin A1a/A1b.

EXAMPLE 5

4''-[(Ethoxycarbonyl)methyl]-22,23-Dihydroavermectin B1a/B1b

To a suspension of the zinc-copper couple (prepared as in Example 1) in 2 ml of dry tetrahydrofuran, 200 mg of 4''- keto-22,23-dihydroavermectin B1a/B1b and 30 μl of ethyl bromoacetate is added. The reaction mixture is heated at reflux under nitrogen until the reaction is judged to be complete by thin layer chromatography on silica gel. Addition of excess ethyl bromoacetate is periodically required to maintain a convenient reaction rate and to force the reaction to completion. The heterogeneous reaction mixture is filtered into 10 ml of saturated ammonium chloride solution. The aqueous mixture is then repeatedly extracted with ethyl acetate. The organic extracts are back-washed with water and brine and then dried with sodium sulfate. Concentration of this organic solution gives the crude product. Preparative thin layer chromatography on silica gel affords pure 4''-[(ethoxycarbonyl)methyl]-22,23dihydroavermectin B1a/B1b.

EXAMPLE 6

4'',23-Diketo-5-O-(tert.-butyldimethylsilyl)avermectin B2a/B2b

To a solution of oxalyl chloride (114 μl) in 1.5 ml of dry methylene chloride at −60° C. under nitrogen, a solution of dimethylsulfoxide (DMSO) (185 μl) in 1 ml of methylene chloride is added. The reaction mixture is stirred for five minutes at −60° C. and a solution of 5-O-(tert.-butyldimethylsilyl)avermectin B2a/B2b (300 mg) in 2.0 ml of methylene chloride is added over a few minutes. The reaction mixture is stirred for 30 minutes at −60° C. after which 0.82 ml of triethylamine is added and the resulting mixture permitted to warm to room temperature. The reaction mixture is diluted with 45 ml of water and the resulting layers separated. The aqueous layer is repeatedly extracted with methylene chloride. The combined organic phases are back-washed with 0.5N hydrochloric acid, 5% aqueous sodium bicarbonate solution, water, and brine. The organic solution is dried with sodium sulfate, concentrated, and chromatographed on silica gel to give 4'',23-diketo-5-O-(tert.-butyldimethylsilyl)avermectin B2a/B2b.

EXAMPLE 7

4''-(Ethoxycarbonyl)methyl]-23-keto-avermectin B2a/B2b

To a suspension of the zinc-copper couple (prepared as in Example 1) in 2ml of dry tetrahydrofuran, 100 mg of 4'',23-diketo-5-O-(tert.-butyldimethylsilyl)avermectin B2a/B2b and 15 μl of ethyl bromoacetate is added. The reaction mixture is heated at reflux under an inert atmosphere such as nitrogen or argon. Additional ethyl bromoacetate is added as required until all starting material has disappeared as judged by thin layer chromatography on silica gel. The heterogeneous reaction mixture is then filtered into 20 ml of saturated ammonium chloride solution. The aqueous mixture is repeatedly extracted with ethyl acetate. The organic extracts are back-washed with water and brine and then dried with sodium sulfate or magnesium sulfate. Concentration of this organic solution gives the crude product. The crude product was desilylated with excess HF-pyridine reagent in tetrahydrofuran (see Example 3). Appropriate workup and preparative thin layer chromatography on silica gel affords pure 4''-[(ethoxycarbonyl)methyl]-23-keto-avermectin B2a/B2b as a mixture of diastereomers.

EXAMPLE 8

4''-[(Ethoxycarbonyl)methyl]-avermectin B2a/B2b

To a solution of 16 mg of 4''-[(ethoxycarbonyl)methyl]-23-keto-avermectin B2a/B2b in 0.5 ml of anhydrous ethanol, 7 mg of sodium borohydride is added. The reaction mixture is stirred for 6 hr at room temperature at which point 0.5 ml of acetone is added to quench excess reducing agent. The mixture is stirred for 0.5 hr and then diluted with ethyl acetate (30 ml). This solution is then washed with 0.5N hydrochloric acid, water, 5% sodium bicarbonate solution and brine. The organic phase is dried with sodium sulfate, concentrated, and purified by preparative thin layer chromatography to give 4''-[(ethoxycarbonyl)methyl]avermectin B2a/B2b.

EXAMPLE 9

4''-(Benzyloxycarbonyl)methyl]-avermectin B1a/B1b

To a suspension of the zinc-copper couple (prepared as in Example 1) in 2.5 ml of dry tetrahydrofuran, 125 mg of 4''-keto-avermectin B1a/B1b and 20 μl of benzyl bromoacetate is added. The reaction mixture is heated at reflux under argon. Additional benzyl bromoacetate is added as required until all starting material has disappeared as judged by thin layer chromatography on silica gel. The heterogeneous reaction mixture is then filtered into 20 ml of saturated ammonium chloride solution. The aqueous mixture is repeatedly extracted with ethyl acetate. The organic extracts are then back-washed with water and brine and dried with magnesium sulfate. Concentration of this organic solution gives the crude product. Preparative thin layer chromatography on silica gel affords pure 4''-[(benzyloxycarbonyl)methyl]-avermectin B1a/B1b as a mixture of diastereomers.

EXAMPLE 10

4''-[1-(Ethoxycarbonyl)ethyl]-avermectin B1a/B1b

To a suspension of the zinc-copper couple (prepared as in Example 1) in 2 ml of dry tetrahydrofuran, 100 mg of 4''-keto-avermectin B1a/B1b and 20 μl of ethyl 2-bromopropionate is added. The reaction mixture is heated at reflux under nitrogen. Periodically additional ethyl 2-bromopropionate is added as required until all starting material has disappeared as judged by thin layer chromatography on silica gel. The heterogeneous reaction mixture is then filtered into 30 ml of saturated ammonium chloride solution. The aqueous mixture is repeatedly extracted with ethyl acetate. The organic extracts are then back-washed with water and brine and dried with magnesium sulfate. Concentration of this organic solution gives the crude product. Preparative thin layer chromatography on silica gel affords pure 4''-[1-(ethoxycarbonyl)ethyl]-avermectin B1a/B1b as a mixture of diastereomers.

EXAMPLE 11

4''-[(Ethoxycarbonyl)fluoromethyl]-22,23-dihydroayermectin B1a/B1b

To a suspension of the zinc-copper couple (prepared as in Example 1) in 3 ml of dry tetrahydrofuran, 150 mg of 4''-keto-22,23-dihydroavermectin B1a/B1b and 25 μl of ethyl bromofluoroacetate is added. The reaction mixture is heated at reflux under nitrogen until all starting material has disappeared as judged by thin layer chromatography on silica gel. Periodically additional ethyl bromofluoroacetate is added as required to complete the reaction. The heterogeneous reaction mixture is then filtered into 30 ml of saturated ammonium chloride solution. The aqueous mixture is repeatedly extracted with ethyl acetate. The organic extracts are then back-washed with water and brine and dried with sodium sulfate. Concentration of this organic solution gives the crude product. Preparative thin layer chromatography on silica gel affords pure 4''-[(ethoxycarbonyl)fluoromethyl]22,23-dihydroavermectin B1a/B1b as a mixture of diastereomers.

EXAMPLE 12

4''-(Carboxy)methyl]-avermectin B1a/B1b

A solution of aluminum chloride (120 mg) in 1 ml of nitromethane is added to a cold (0° C.) solution of 100 mg of 4''-[(benzyloxycarbonyl)methyl]avermectin B1a/B1b and 300 mg of anisole in 1 ml of methylene chloride. The reaction mixture is then stirred at room temperature until thin layer chromatography on silica gel indicates near complete reaction. The reaction mixture is diluted with 30 ml of ethyl acetate and the resulting solution washed with 10 ml of cold 0.5N hydrochloric acid. The organic phase is then thoroughly washed with water and dried over sodium sulfate. Concentration of the organic layer affords the crude product which is purified on a HP-20 column with aqueous methanol to provide pure 4''-[(carboxy)methyl]-avermectin B1a/B1b.

EXAMPLE 13

4''-[(Ethoxycarbonyl)methyl]-5-Acetyl-22,23-Dihydroavermectin B1a/B1b

To a cold (0° C.) solution of 4''-[(ethoxycarbonyl)methyl]-22,23-dihydroavermectin B1a/B1b (75 mg) in 5 ml of pyridine, excess acetic anhydride (50 mg) is added. The reaction mixture is then stirred at 0° C. for 6 hours before pouring it into 50 ml of cold water. The mixture is extracted repeatedly with ethyl acetate. The combined organic layers are washed with cold 0.5N hydrochloric acid, water, 5% aqueous sodium bicarbonate and brine before drying with anhydrous sodium sulfate. The organic solution is concentrated under reduced pressure and purified by preparative thin layer chromatography to afford 4''-[(ethoxycarbonyl)methyl]-5-acetyl-22,23-dihydroavermectin B1a/B1b.

EXAMPLE 14

13-[(Ethoxycarbonyl)methyl]-22,23-Dihydroavermectin B1a/B1b Aglycone

To a suspension of the zinc-copper couple (prepared as in Example 1) in 2 ml of dry tetrahydrofuran, 150 mg of 13-keto-22,23-dihydroavermectin B1a/B1b aglycone and 25 μl of ethyl bromoacetate is added. The reaction mixture is heated under nitrogen. Periodically, additional ethyl bromoacetate is added to the reaction mixture in order to force the reaction to completion as judged by thin layer chromatography on silica gel. The reaction mixture is filtered into 10 ml of saturated ammonium chloride solution. This mixture is then repeatedly extracted with ethyl acetate. The combined organic layers are back-washed with water and brine and then dried with sodium sulfate. Concentration of this organic solution gives the crude product which upon purification by preparative thin layer chromatography affords 13-[(ethoxycarbonyl)methyl]-22,23-dihydroavermectin B1a/B1b aglycone.

What is claimed is:

1. A compound having the formula:

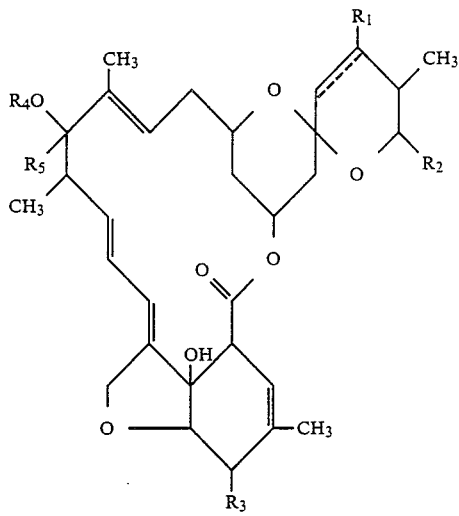

wherein the broken line indicates a single or a double bond;
wherein
$R_1$ is H, loweralkanoyloxy, OH or $=$O provided that is present only when the broken line indicates a single bond;
$R_2$ is isopropyl or sec-butyl;
$R_3$ is OH, $OCH_3$ or loweralkanoyloxy;
$R_4$ is H,

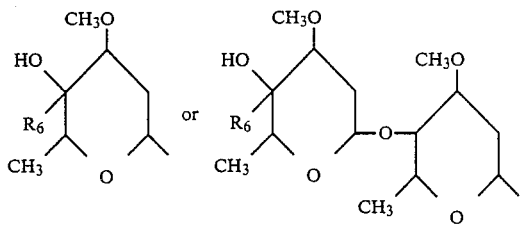

$R_5$ is hydrogen or $R_6$ provided that $R_5$ is hydrogen only when $R_4$ is other than hydrogen;
$R_6$ is $R_7O_2C-CH_2-$, $R_7O_2CCHF-$, $R_7O_2CCF_2-$ or $R_7O_2CCH(Alk)-$ where Alk is loweralkyl or phenylloweralkyl; and
$R_7$ is hydrogen, loweralkyl, phenylloweralkyl, or substituted phenylloweralkyl wherein the substituents are loweralkyl or halogen; and the 5-position tri(loweralkyl)silyl protected hydroxy derivatives thereof.

2. A method for the treatment of parasitic infections which comprises administering to an animal infected with parasites an effective amount of a compound of claim 1.

3. A composition useful for treating animals infected with parasites or areas infested with parasites which co an inert carrier and an effective amount of a compound of claim 1.

4. A method for the treatment of insect infestations which comprises treating the area of such insect infestation with an effective amount of a compound of claim 1.

* * * * *